United States Patent
Karnam

(10) Patent No.: US 10,575,794 B2
(45) Date of Patent: Mar. 3, 2020

(54) SYSTEM FOR SUPERVISING AN OCCUPANT OF A WHEELCHAIR

(71) Applicants: SRM UNIVERSITY, Chennai (IN); Sunitha Anantha Karnam, Khandavalli (IN)

(72) Inventor: Sunitha Anantha Karnam, Khandavalli (IN)

(73) Assignee: SRM UNIVERSITY, Chennai ( * ) Notice: Subject to any disclaimer, the term of this patent is extended or adjusted under 35 U.S.C. 154(b) by 0 days.

(21) Appl. No.: 15/928,422

(22) Filed: Mar. 22, 2018

(65) Prior Publication Data
US 2018/0271457 A1 Sep. 27, 2018

(30) Foreign Application Priority Data
Mar. 27, 2017 (IN) .............................. 201741010844

(51) Int. Cl.
| | | |
|---|---|---|
| *A61G 5/10* | (2006.01) | |
| *A61B 5/0205* | (2006.01) | |
| *A61B 5/11* | (2006.01) | |
| *A61B 5/021* | (2006.01) | |

(Continued)

(52) U.S. Cl.
CPC ............ *A61B 5/746* (2013.01); *A61B 5/0022* (2013.01); *A61B 5/02055* (2013.01); *A61B 5/1113* (2013.01); *A61G 5/10* (2013.01); *A61B 5/021* (2013.01); *A61B 5/024* (2013.01); *A61G 2203/12* (2013.01); *A61G 2203/14* (2013.01); *A61G 2203/16* (2013.01); *A61G 2203/36* (2013.01); *A61G 2203/40* (2013.01);

(Continued)

(58) Field of Classification Search
CPC ... A61B 5/746; A61B 5/0022; A61B 5/02055; A61B 5/1113; A61B 5/021; A61B 5/024; A61G 2203/12; A61G 2203/14; A61G 2203/16; A61G 2203/36; A61G 2203/46; A61G 2203/70; A61G 5/10
See application file for complete search history.

(56) References Cited

U.S. PATENT DOCUMENTS

| | | | | |
|---|---|---|---|---|
| 2005/0083207 A1* | 4/2005 | Smith | ................... | A61F 5/3776 340/668 |
| 2008/0135321 A1* | 6/2008 | Ripple | ................... | A61G 5/043 180/282 |

(Continued)

*Primary Examiner* — Benyam Haile
*Assistant Examiner* — Mancil Littlejohn, Jr.
(74) *Attorney, Agent, or Firm* — The Roy Gross Law Firm, LLC; Roy Gross

(57) ABSTRACT

A system (100) for supervising an occupant of a wheelchair relates to the field of electronics engineering. The system (100) enables an authorized person to effectively supervise the occupant. The system (100) further enables the occupant to control electrical appliances. The system (100) includes a plurality of sensors (102) configured to sense various parameters related to the occupant and the wheelchair. The sensed parameters are stored in a server (108), which enables the authorized person to effectively supervise the occupant and take necessary actions in case of the health of the occupant deteriorates. The system (100) also enables the authorized person to track the wheelchair, and to locate the wheelchair if the wheelchair meets an accident. Further, the system (100) enables the occupant to control the electrical appliances while sitting on the wheelchair.

10 Claims, 1 Drawing Sheet

(51) Int. Cl.
*A61B 5/024* (2006.01)
*A61B 5/00* (2006.01)

(52) U.S. Cl.
CPC ...... *A61G 2203/46* (2013.01); *A61G 2203/70* (2013.01); *A61G 2203/726* (2013.01)

(56) References Cited

U.S. PATENT DOCUMENTS

| | | | | |
|---|---|---|---|---|
| 2012/0136666 | A1* | 5/2012 | Corpier | H04L 12/2829 704/275 |
| 2014/0206307 | A1* | 7/2014 | Maurer | H04W 4/90 455/404.2 |
| 2015/0137997 | A1* | 5/2015 | Huang | A61B 5/1112 340/870.09 |
| 2017/0032648 | A1* | 2/2017 | McClain | G08B 21/043 |

* cited by examiner

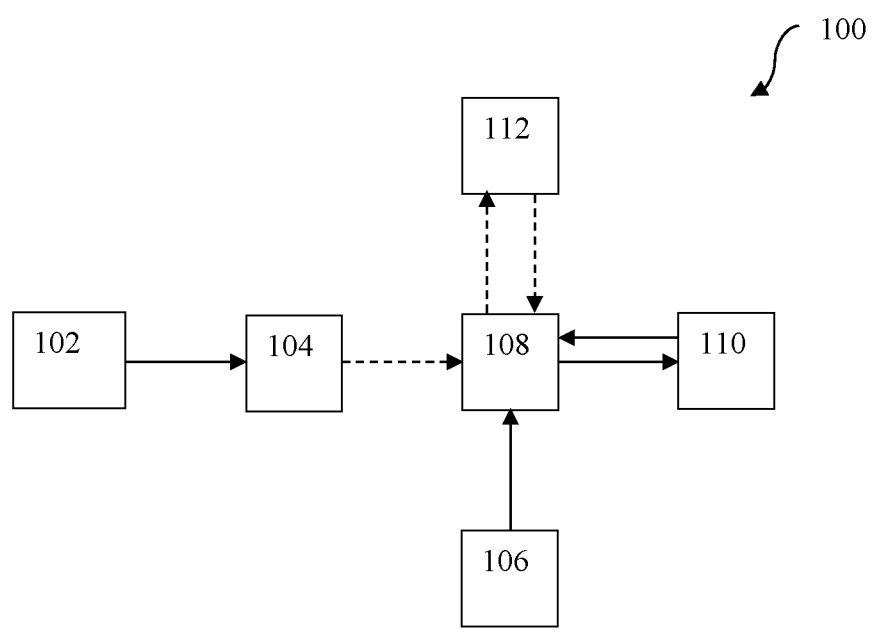

SYSTEM FOR SUPERVISING AN OCCUPANT OF A WHEELCHAIR

FIELD

The present disclosure relates to the field of electronics engineering. Particularly, the present disclosure relates to the field of wheelchairs.

BACKGROUND

Conventionally, wheelchairs are used by persons having limited mobility or having any health condition. Typically, the person using a wheelchair should be under continuous medical supervision to monitor health condition of the person. However, it is a tedious task for a person having limited mobility to visit a doctor every time for medication. Further, the conventional wheelchairs do not provide continuous monitoring of parameters associated with health of a person. Furthermore, the conventional wheelchairs are not configured to control electrical appliances, thereby restricting access to the person. Further, such wheelchairs are unable to provide a clear rear view to the occupant which may lead to accidents while reversing the wheelchair.

Therefore, there is felt a need of a system for an occupant of the wheelchair that alleviates abovementioned drawbacks.

OBJECTS

Some of the objects of the present disclosure, which at least one embodiment herein satisfies, are as follows:

An object of the present disclosure is to provide a system for an occupant of a wheelchair that allows a doctor to effectively and continuously monitor and supervise health parameters of the occupant.

Another object of the present disclosure is to provide a system for supervising an occupant of a wheelchair that is safe to use by the occupant.

Another object of the present disclosure is to provide a system for supervising an occupant of a wheelchair that requires less manufacturing cost.

Other objects and advantages of the present disclosure will be more apparent from the following description, which is not intended to limit the scope of the present disclosure.

SUMMARY

The present disclosure envisages a system for supervising an occupant of a wheelchair. The system comprises a set of sensors, a processor, a memory, a server, a database, and a user device. The set of sensors is configured to sense a plurality of parameters related to the occupant and the wheelchair. The set of sensors is further configured to generate a plurality of digital signals corresponding to each of the plurality of parameters. The processor is cooperating with the set of sensors to receive the plurality of digital signals. The processor is adapted to generate digital values corresponding to the digital signals. The memory is configured to store a pre-determined set of reference values defining a range corresponding to each of the parameters. In a preferred embodiment, the set of reference values includes values corresponding to the health parameters, and reference distance between the wheelchair and an obstacle. The server is cooperating with the processor and the memory to receive the digital values and the reference values respectively. The server is adapted to compare the digital values with the reference values to generate an alerting signal. In a preferred embodiment, the alerting signal is generated when the digital values do not fall within the range of reference values. The database is cooperating with the server to store the digital values. The user device is configured to cooperate with the server to receive the alerting signals thereby enabling an authorized person to supervise the occupant and take necessary actions. In an embodiment, the authorized person is selected from a group consisting of a doctor, a caretaker, a physician, and any combinations thereof.

In a preferred embodiment, the server is a cloud server cooperating with the processor via a network.

In another embodiment, the set of sensors is configured to measure health parameters of the occupant, wherein the health parameters are selected from a group consisting of pulse, body temperature, blood pressure, and any combinations thereof.

In yet another embodiment, the set of sensors includes an accelerometer, a location sensor, and a plurality of ultrasonic sensors. The accelerometer is configured to sense movement of the wheelchair, and adapted to transmit digital signals, if the wheelchair meets an accident. The location sensor is configured to sense location of the wheelchair. The plurality of ultrasonic sensors is disposed at an operative back side of the wheelchair, and configured to sense distance between the wheelchair and an obstacle.

The system further includes an input module configured to accept input signals from the occupant to control electrical appliances. In an embodiment, the input module is selected from a group consisting of a joystick, a touchscreen, an android based application, and any combinations thereof.

BRIEF DESCRIPTION OF THE ACCOMPANYING DRAWING

A system for supervising an occupant of a wheelchair, of the present disclosure, will now be described with the help of the accompanying drawing, in which:

FIG. 1 illustrates a block diagram of the system for supervising an occupant of a wheelchair, in accordance with an embodiment of the present disclosure.

LIST OF REFERRAL NUMERALS

100—System
102—Set of sensors
104—Processor
106—Memory
108—Server
110—Database
112—User device

DETAILED DESCRIPTION

A system for supervising an occupant of a wheelchair, of the present disclosure, will now be described with reference to the embodiments of the present disclosure.

The system for supervising an occupant of a wheelchair is now described with reference to FIG. 1.

FIG. 1 illustrates a block diagram of the system for supervising an occupant of a wheelchair (hereinafter referred to as system), in accordance with an embodiment of the present disclosure.

A system 100 comprises a set of sensors 102, a processor 104, a memory 106, a server 108, a database 110, and a user device 112.

The set of sensors 102 is configured to sense a plurality of parameters. The plurality of parameters is related to an occupant (not shown in figure) and a wheelchair (not shown in figures). The set of sensors 102 is further configured to generate a plurality of digital signals corresponding to each of the plurality of parameters.

The set of sensors 102 includes a pulse sensor, a temperature sensor, and a blood pressure sensor. The pulse sensor is configured to sense pulse of the occupant. The temperature sensor is configured to sense body temperature of the occupant. The blood pressure sensor is configured to sense blood pressure of the occupant.

In an embodiment, the set of sensors 102 is configured to measure health parameters of the occupant. The health parameters are selected from the group consisting of pulse, body temperature, blood pressure, and any combination thereof.

The processor 104 is cooperating with the set of sensors 102. The processor is configured to receive the plurality of digital signals generated by the set of sensors 102. The processor 104 is adapted to generate digital values corresponding to each of the digital signals.

The memory 106 is configured to store a pre-determined set of reference values corresponding to the plurality of parameters sensed by the set of sensors 102. The pre-determined set of reference values includes a range of reference values corresponding to the each of plurality of parameters.

In an embodiment, the set of reference values is the ideal values corresponding to each of the health parameters of the occupant of the wheelchair. In another embodiment, the set of reference values includes the health parameters including, but not limited to, pulse, body temperature, body pressure, and blood pressure.

In yet another embodiment, the set of reference values include a reference distance between the wheelchair and an obstacle. The reference distance is the minimum distance that must be maintained between the wheelchair and the obstacle in order to avoid any accident therebetween.

The server 108 is cooperating with the processor 104 and the memory 106. The server receives the generated digital values. Further, the server 108 is configured to fetch the set of reference values from the memory 106. The server 108 is adapted to compare the received digital values with the received reference values and generate an alerting signal. In an embodiment, the alerting signal is generated only when the digital values do not fall within the range of reference values.

In a preferred embodiment, the server 108 is a cloud server cooperating with the processor 104 via a wireless network. Typically, a network interface unit (not shown in figures) is used to establish a connection between the processor 104 and the server 108.

In an embodiment, the server comprises an alerting module (not shown in figures). The alerting module is configured to receive the alerting signal from the server 108. The alerting module is further configured to transmit the alerting signal to the user device 112. The alerting signal is in the form of a sound, a text message, vibrations or any combinations thereof.

The database 110 is cooperating with the server 108, and configured to store the digital values generated by the processor 104. In an embodiment, the database 110 is configured to store the health parameters of the occupant of the wheelchair.

The user device 112 is configured to cooperate with the server 108. The user device is further configured to receive the alerting signal generated by the server 108, thereby enabling an authorized person using the user device 112 to effectively supervise the occupant and take necessary actions.

In an embodiment, the authorized person is a person selected from a group consisting of a doctor, a caretaker, and a physician. In a preferred embodiment, the authorized person is a doctor of the occupant, who receives the alerting signal and takes the necessary actions.

In an operative configuration, the set of sensors 102 senses the health parameters of the occupant. The set of sensors 102 typically detects pulse, body temperature, and the blood pressure of the occupant. Each of the set of sensors 102 generates digital signal corresponding to the health parameter sensed by it. The digital signals are then received by the processor 104. The processor 104 converts the digital signals into corresponding digital values and transmits the digital values to the server 108 via a network, wherein the server is a cloud server. The server 108 receives the digital values and stores the same in the database 110. As the sensed health parameters are stored in the database 110 of the server 108, which is a cloud server, the health of the occupant can be monitored from any place in the world.

Further, the server 108 compares the digital values with the reference values received from the memory 106. The server 108 generates an alerting signal only if the digital value associated with a particular health parameter does not fall within the range of pre-determined reference value of that particular parameter. The alerting module receives the generated alerting signal and transmits to the user device 112, which is accessed by the authorized person, preferably a doctor. The doctor can observe the health condition of the occupant using the server 108 and prescribe required medication to control the particular parameter.

The system 100 enables the authorized person to retrieve all the measured health parameters that are stored in the database 110 previously using the server 108 anytime from any place in the world.

The set of sensors 102 further includes an accelerometer, a location sensor, and a plurality of ultrasonic sensors.

The accelerometer is disposed on the wheelchair and configured to sense movement of the wheelchair. The accelerometer is adapted to transmit digital signals, if the wheelchair meets an accident. The location sensor is disposed on the wheelchair and is configured to sense the location of the wheelchair. The location sensor is further configured to generate digital signals corresponding to the location of the wheelchair. The location of the wheelchair is fed to the server 108 via the processor 104, thereby enabling the authorized person to locate and track the wheelchair. The plurality of ultrasonic sensors is disposed at an operative back side of the wheelchair, and is configured to sense distance between the wheelchair and any obstacle that may obstruct the path of the wheelchair while reversing or moving the wheelchair.

In a preferred embodiment, the location sensor is a GPS sensor.

The system 100 further includes an input module (not shown in figures) that is configured to accept input signals from the occupant so as to control electrical appliances. In an embodiment, the input module is selected from a group consisting of a joystick, a touchscreen, an android based application, and any combinations thereof.

In an operative configuration, the accelerometer transmits digital signals when the wheelchair meets an accident or fells down. The digital signals are received by the server 108. The server 108 communicates with the location sensor to receive the location of the wheelchair. The location, in the form of text message, is then transmitted to the authorized person by the server 108 using the alerting module.

In an embodiment, a first controller (not shown in figures) is disposed on the wheelchair, and is configured to receive the digital signals from the accelerometer and triggers the GSM module to send an alert text message to the authorized person, preferably a caretaker.

The plurality of ultrasonic sensors detects any obstacle approaching the wheelchair. The plurality of ultrasonic sensors then generates obstacle signals having information regarding distance between each obstacle and the wheelchair. The obstacle signals are received by the processor 104. The processor generates the digital values corresponding to the obstacle signals. The digital values corresponding to the obstacle signals are then transmitted to the server 108. The server 108 compares the digital values with the reference values fetched from the memory 106. If the digital value is lesser than the reference distance value, it means that the obstacle is within the minimum distance which may cause an accident. In such conditions, the server 108 triggers an alarm to warn the occupant and the wheelchair is stopped.

In an embodiment, obstacle signal is transmitted to the first controller and reference distance is fed to the controller. If the obstacle comes closer to the wheelchair, i.e., within the reference distance, the controller triggers the alarm and stops the wheelchair.

The system 100 is further configured to control the electrical appliances. The input module (not shown in figures) receives inputs regarding controlling the electrical appliances. The inputs are then fed to the first controller which is cooperating with the second controller via a Bluetooth channel. The inputs are fed to the second controller via a first controller. The second controller triggers a relay switch to control the appliances corresponding to the inputs received.

The system 100 enables the doctor and the caretaker to effectively supervise the occupant. As the health of the occupant is monitored using several sensors, the doctor can view the health status of the occupant from anywhere in the world and can guide him accordingly. Further, the system 100 enables the caretaker to continuously track the wheelchair.

The system 100 further enables the occupant of the wheelchair to control the electrical appliances.

TECHNICAL ADVANCEMENTS

The present disclosure described herein above has several technical advantages including, but not limited to, the realization of a system for supervising an occupant of a wheelchair that:
  allows a doctor to effectively and continuously monitor and supervise health parameters of the occupant;
  is safe to use by the occupant; and
  requires less manufacturing cost.

The disclosure has been described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully revealed the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A system for supervising an occupant of a wheelchair, said system comprising:
  a set of sensors configured to sense a plurality of parameters related to said occupant and said wheelchair, and generate a plurality of digital signals corresponding to each of said plurality of parameters, wherein said set of sensors comprises:
    an accelerometer configured to sense movement of said wheelchair and adapted to generate and transmit digital signals, if said wheelchair meets an accident;

a location sensor configured to sense location of said wheelchair; and a plurality of ultrasonic sensors disposed at an operative back side of said wheelchair, and configured to sense distance between said wheelchair and an obstacle;

a first controller disposed on said wheelchair, and configured to receive the digital signals transmitted by said accelerometer, said first controller configured to trigger said location sensor to receive said sensed location of said wheelchair, and further configured to send an alert text message including said sensed location to an authorized user;

a processor cooperating with said set of sensors to receive said plurality of generated digital signals and adapted to generate digital values corresponding to each of said generated digital signals;

a memory configured to store a pre-determined set of reference values defining a range corresponding to each of said plurality of parameters;

a server cooperating with said processor and said memory to receive said generated digital values and said reference values respectively, and adapted to compare said digital values with said reference values to generate an alerting signal, said server further configured to generate a trigger signal to stop said wheelchair and alert said occupant of the wheelchair when said digital value corresponding to sensed distance between said wheelchair and said obstacle is lesser than said reference value;

a database cooperating with said server to store said digital values; and a user device configured to cooperate with said server to receive said alerting signals, and further configured to cooperate with said first controller to receive alert text message, thereby enabling said authorized person to supervise said occupant and take necessary actions.

2. The system as claimed in claim 1, wherein said set of sensors includes:
a pulse sensor configured to sense pulse of said occupant;
a temperature sensor configured to sense body temperature of said occupant; and
a blood pressure sensor configured to sense blood pressure of said occupant.

3. The system as claimed in claim 1, wherein said server is a cloud server cooperating with said processor via a network.

4. The system as claimed in claim 1, wherein said set of reference values includes values corresponding to said health parameters, and reference distance between said wheelchair and an obstacle.

5. The system as claimed in claim 1, wherein said alerting signal is generated when said digital values do not fall within said range of reference values.

6. The system as claimed in claim 1, wherein said authorized person is selected from a group consisting of a doctor, a caretaker, a physician, and any combinations thereof.

7. The system as claimed in claim 1, wherein said location sensor is a GPS sensor.

8. The system as claimed in claim 1, which includes an input module configured to accept input signals from said occupant to control electrical appliances.

9. The system as claimed in claim 8, wherein said input module is selected from a group consisting of a joystick, a touchscreen, an android based application, and any combinations thereof.

10. The system as claimed in claim 1, which enables said authorized user to retrieve said stored digital values corresponding to parameters via said user device.

* * * * *